United States Patent [19]
Spehalski

[11] Patent Number: 6,099,513
[45] Date of Patent: Aug. 8, 2000

[54] WOUND DRAIN WITH ALTERNATING PERIMETRICALLY ARRANGED LUMENS AND DUCTS

[75] Inventor: Stephen R. Spehalski, Gurnee, Ill.

[73] Assignee: Allegiance Corporation, McGaw Park, Ill.

[21] Appl. No.: 08/709,206

[22] Filed: Aug. 27, 1996

[51] Int. Cl.$^7$ .................................................. A61M 25/00
[52] U.S. Cl. ......................... 604/264; 604/93; 604/280
[58] Field of Search ................................ 604/27, 35, 30, 604/39, 43, 45, 49, 93, 102, 105, 126, 128, 129, 173, 175, 266, 282, 264, 268, 280, 180, 902

[56] References Cited

U.S. PATENT DOCUMENTS

| | | | |
|---|---|---|---|
| 3,590,820 | 7/1971 | Nehra et al. | 128/276 |
| 4,398,910 | 8/1983 | Blake et al. | 604/93 |
| 4,465,481 | 8/1984 | Blake | 604/280 |
| 4,508,533 | 4/1985 | Abramson | 604/35 |
| 4,523,920 | 6/1985 | Russo | 604/93 |
| 4,573,965 | 3/1986 | Russo | 604/30 |
| 4,650,463 | 3/1987 | LeVeen et al. | 604/43 |
| 4,717,379 | 1/1988 | Ekholmer | 604/43 |
| 5,116,310 | 5/1992 | Seder et al. | 604/43 |
| 5,360,414 | 11/1994 | Yarger | 604/264 |
| 5,562,622 | 10/1996 | Tihon | 604/105 |

Primary Examiner—Corrine M. McDermott
Assistant Examiner—Cris L. Rodriguez
Attorney, Agent, or Firm—Kay H. P. Hannafan

[57] ABSTRACT

A implantable wound drain device includes an annular outer wall, a central core defining at least one longitudinal axis and being disposed within and spaced radially inwardly from the outer wall, and radial inner walls disposed within the outer wall and extending between and connected to the central core and outer wall such that adjacent pairs of the inner walls together with the outer wall form a plurality of elongated lumens for draining fluids therefrom from the wound. The lumens are circumferentially spaced from one another about and extend along the longitudinal axis such that the inner walls are disposed between adjacent pairs of the lumens. Each inner wall has an elongated duct defined therein extending along the longitudinal axis and extending outwardly from adjacent to the central core to the outer wall and define an entrance to the duct through the outer wall to permit fluid flow from the wound exteriorly of the outer wall through the entrance and into the duct. Thus, each duct is disposed in a respective one of the inner walls disposed between the adjacent pairs of lumens. Also, one or more interior portals may be defined in spaced apart relation from each other through at least the inner walls adjacent to the central core and preferably also through the central core.

15 Claims, 4 Drawing Sheets

WOUND DRAIN WITH ALTERNATING PERIMETRICALLY ARRANGED LUMENS AND DUCTS

TECHNICAL FIELD

The present invention generally relates to devices for providing post-surgical draining of exudate from a closed surgical site or wound and, more particularly, is concerned with an implantable wound drain having a plurality of enclosed lumens and open ducts extending longitudinally and alternating with each other in a perimetrical arrangement.

BACKGROUND ART

A wound resulting from a surgical procedure or the like often produces fluid, commonly referred to as exudate, which needs to be drained away from the wound site for proper healing and recovery of the wound. Wounds of this nature either are closed at the end of the surgical procedure or will close in the course of the body's natural healing process. Closure of the wound creates a need for a means to drain the fluid therefrom to promote satisfactory healing. A variety of catheter drain devices have been developed over the years to address this need.

Wound drain devices have typically comprised a drain section of a length of tubing perforated with small holes through the tubing wall. Fluid from the wound enters the tubing through the small holes and travels away from the wound within the tubing lumen. Problems exist, however, with this basic solution, including the likelihood of the tubing lumen clogging on the one hand with debris and/or new tissue ingrowth entering through the small holes and on the other hand by structural weakness in the walls of the tubing forming kinks and the like.

The above-mentioned inadequacies of the basic wound drain device have encouraged the development of a variety of improved designs. U.S. Pat. No. 4,398,910 to Blake et al. discloses a wound drain device having a central core with four strut portions projecting radially therefrom. The strut portions are equal in size and are spaced at equal angles relative to one another. The periphery of the wound drain is in the form of a plurality of overhang portions provided at the end of each of the four strut portions, thereby forming four T-shaped members. The overhang and strut portions cooperate to form four longitudinal lumens extending the length of the drain. Gaps between the overhang portions permit fluid entry into the lumens and are sized to inhibit new tissue from growing and debris from passing therethrough. The Blake et al. wound drain device, in comparison to other prior art drains, has increased tissue contact and luminal flow drainage areas designed to increase the level of drainage and to prevent clogging in the draining process and has an increased drain body cross-sectional area to increase the strength of the drain body. U.S. Pat. No. 4,465,481 to Blake discloses a single piece wound drain catheter, which is intended to improve upon the design disclosed in the above-described patent to Blake et al. (U.S. Pat. No. 4,398,910) by providing a single continuous elongate member of silicone material having a drain segment, a transition tube segment and an extension tube segment. The Blake et al. (U.S. Pat. No. 4,398,910) wound drain device needs to be connected to a separate outflow tube and thus has a point at which the strength of the tubing might be reduced. Problems exist, however, with the Blake et al. (U.S. Pat. No. 4,398,910) and Blake (U.S. Pat. No. 4,465,481) designs in that they allow for a single point location downstream for each longitudinal lumen to clog and do not distribute suction evenly over the length of the drain.

Also, U.S. Pat. No. 4,523,920 to Russo discloses a surgical suction drain device including a pair of spaced apart flanges with a web disposed therebetween having a single longitudinal lumen with apertures formed transversely through the flanges and intersecting the lumen. The problem with this device, however, is that inhibition of proper fluid drainage may be likely to happen by there being only one lumen provided and needed to become clogged.

Other wound draining devices have been developed which provide a fluid suction component. U.S. Pat. No. 4,508,533 to Abramson discloses a surgical drain device with a triple lumen catheter body, a three-tube connector interfit with the catheter body at the proximal end and adapted to provide a suction port, an irrigation port and an air intake port, a suture means to anchor the drain, and a softened portion at the distal end of the catheter body to facilitate insertion of the drain into the body and to reduce pressure to surrounding tissue. A problem exists, however, with having three lumens in this design in that fluid may back up in the second lumen and have the effect of clogging an antibacteria filter connected thereto and the second lumen would lose its effectiveness in providing a venting effect. Three lumens also require a large opening in the wound which may lead to discomfort for the patient. In an attempt to provide a solution to these problems with three lumens, U.S. Pat. No. 4,573,965 to Russo discloses only two lumens in its wound draining device. The first lumen is used for applying suction to a wound area. A check valve element and an antibacteria filter are positioned in-line communication with a second lumen to prevent backflow of fluids through the second lumen into the filter. It is notable that each of these devices with suction components have lumens perforated with holes which provide communication between the lumen and the wound. The problem here is that these holes may have a tendency to lead to the above-mentioned clogging problem of debris and/or new tissue ingrowth within one of the lumens.

Furthermore, U.S. Pat. No. 4,650,463 to LeVeen et al. discloses a perforated tubing for surgical drainage applications and the like. The tubing is comprised of a body having a central passageway in a clover-leaf cross-sectional appearance with four longitudinally extending grooves spaced at ninety degree arcuate intervals about the body. Perforations interconnect the grooves with the passageway. The perforations are in the form of a series of holes in the bottoms of the grooves. The perforations provide a means of more even distribution of suction over the length of the tubing. Problems exist, however, with this design in that several components are required to make it functional to support compression of tissue and the inhibition of proper fluid drainage may be likely to happen by there being only one lumen provided and needed to become clogged.

Another design, U.S. Pat. No. 5,116,310 to Seder et al., discloses a wound drain catheter formed by multiple parallel lumens to convey fluid from a wound. The design includes holes and at least one longitudinal slot extending interiorly from the outside surface which admits fluids into the lumens and internal holes to divert fluid from blocked lumens. The internal holes allow alternative drainage between lumens. A problem exists, however, with the external holes and slots in that they are susceptible to new tissue ingrowth. Hence, the Seder et al. device is an improvement on the above-mentioned Blake devices relative to drainage but does not alleviate the issues associated with tissue ingrowth.

Consequently, a need still exists for a wound drain which provides an efficient and comprehensive solution to the aforementioned problems in the prior art devices without introducing any new problems in place thereof.

DISCLOSURE OF INVENTION

The present invention provides a wound drain device designed to satisfy the aforementioned need. The wound drain device of the present invention has a plurality of enclosed lumens and a plurality of open ducts which extend longitudinally between distal and proximal ends of the device and alternate with each other in a perimetrical arrangement. In one embodiment where a combination of deep and shallow suction-induced drainage of fluids is desired, no or at least very little cross communication is provided between the enclosed lumens and open ducts so that the application of suction to the lumens and ducts at the proximal end of the device produces "deep" suction-induced drainage via the lumens from the distal end of the device and "shallow" suction-induced drainage via the open ducts along the length of the device. On the other hand in another embodiment where it is more desirable to distribute the suction substantially uniformly along the length of the device, the device is provided with at least one and preferably a plurality of interior portals providing cross communication between the lumens and ducts and being longitudinally spaced from each other so as to define multiple collateral paths for exudate drainage from the open ducts to the enclosed lumens so as to avoid any potential flow blockage problems. The device has an elongated outer wall in one or the other of round and flattened or oblong configurations. The embodiment of the wound drain device having portals best (1) minimizes access of debris and/or new tissue ingrowth which may block any fluid draining through the device, (2) distributes suction substantially evenly along the length of the device, and (3) provides collateral drainage around an occluded lumen. Both embodiments of the wound drain device have structural integrity.

Accordingly, the present invention is directed to a wound drain device for implantation into and drainage of fluid from a wound of a patient. The wound drain device comprises: (a) an elongated tubular body having an elongated annular outer wall defining an exterior surface and having distal and proximal ends; (b) a central core defining at least one longitudinal axis and being disposed within and spaced radially inwardly from the outer wall; and (c) radial inner walls disposed within the outer wall and extending between and connected to the central core and outer wall such that adjacent pairs of the inner walls together with the outer wall form a plurality of elongated enclosed lumens for draining fluids from the wound. The lumens are circumferentially spaced from one another about and extend along the longitudinal axis such that the inner walls are disposed between adjacent pairs of the lumens. Each inner wall has an elongated open duct defined therein extending along the longitudinal axis and extending outwardly from adjacent to the central core to the outer wall and defining an entrance to the duct through the outer wall to permit fluid flow from the wound exteriorly of the outer wall through the entrance and into the duct. Thus, each duct is disposed in a respective one inner wall disposed between each adjacent pair of lumens.

More particularly, each of the ducts is formed by an interior base surface defined in the respective one inner wall adjacent to the central core and by a pair of opposing interior side surfaces defined in the respective one inner wall so as to extend from the interior base surface to the exterior surface of the outer wall and define the elongated entrance to the duct through said outer wall. The entrance to the duct permits fluid flow from the wound exteriorly of the outer wall through the entrance and into the duct. Each of the ducts has a maximum width between the opposing interior side surfaces which is substantially smaller than a maximum width of each of the lumens between the respective adjacent pairs of the inner walls.

In a first embodiment of the wound drain device, there is substantially no cross communication between the enclosed lumens and open ducts. In a second embodiment, the wound drain device comprises at least one and preferably a plurality of interior portals spaced apart from each other and defined at least through the inner walls adjacent to the central core. The portals provide multiple collateral drainage paths for fluid flow from the ducts to the lumens. In the instance where only a few portals are used, they would be disposed near to the distal end of the tubular body.

The portals are disposed closer to the interior base surface of the ducts than to the outer wall and transverse through the inner walls and also preferably through the central core for providing fluid flow from the ducts to the lumens and through the central core to thereby provide the multiple collateral drainage paths for fluid flow. Alternatively, the wound drain device further comprises an elongated lumen formed within, and extending along the longitudinal axis of, the central core.

These and other features and advantages of the present invention will become apparent to those skilled in the art upon a reading of the following detailed description when taken in conjunction with the drawings wherein there is shown and described an illustrative embodiment of the invention.

BRIEF DESCRIPTION OF THE DRAWINGS

In the following detailed description, reference will be made to the attached drawings in which.

BEST MODE FOR CARRYING OUT THE INVENTION

Figure 1:
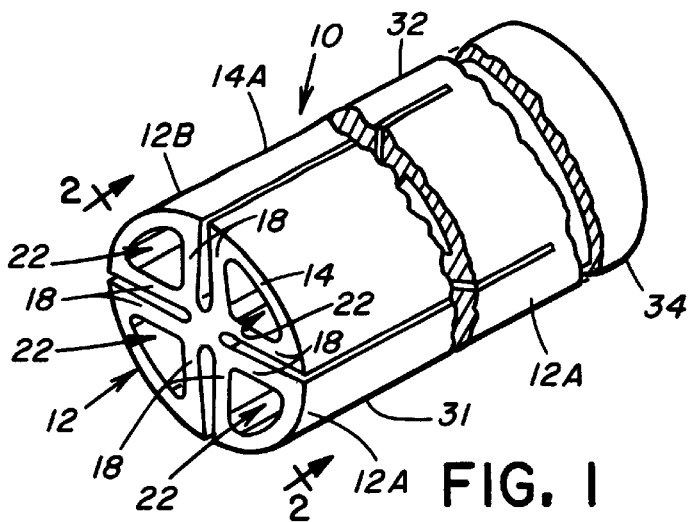
FIG. 1 is a fragmentary perspective view of a first embodiment of the wound drain device of the present invention having a substantially round configuration in cross-section and pluralities of enclosed lumens and open narrow ducts alternating with each other in a perimetrical arrangement but without any interior portals to provide cross communication between the lumens and ducts.
Figure 2:
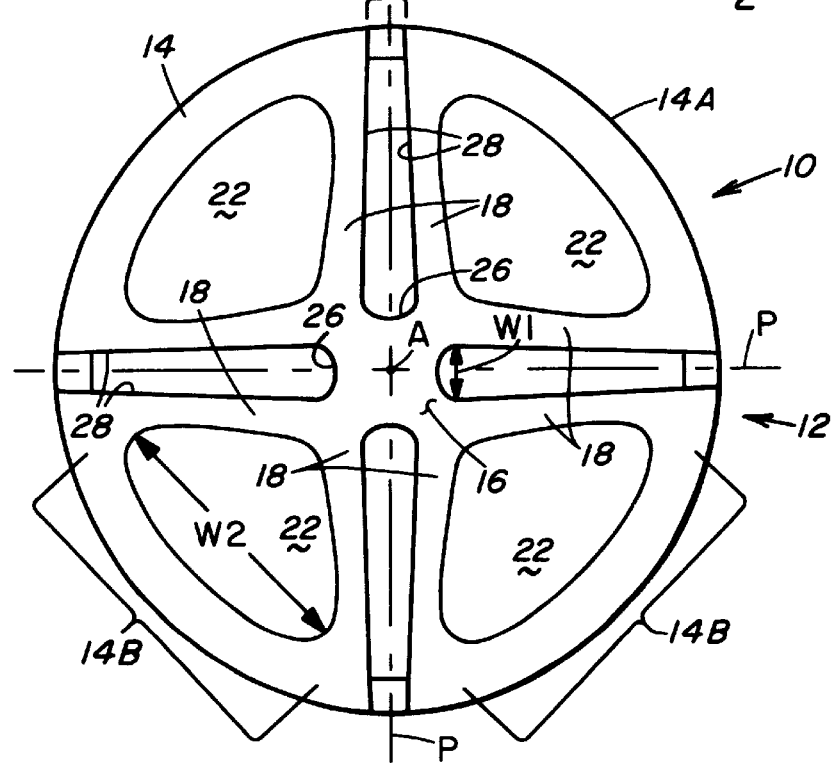
FIG. 2 is an enlarged end elevational view of the device shown in FIG. 1.
Figure 6:
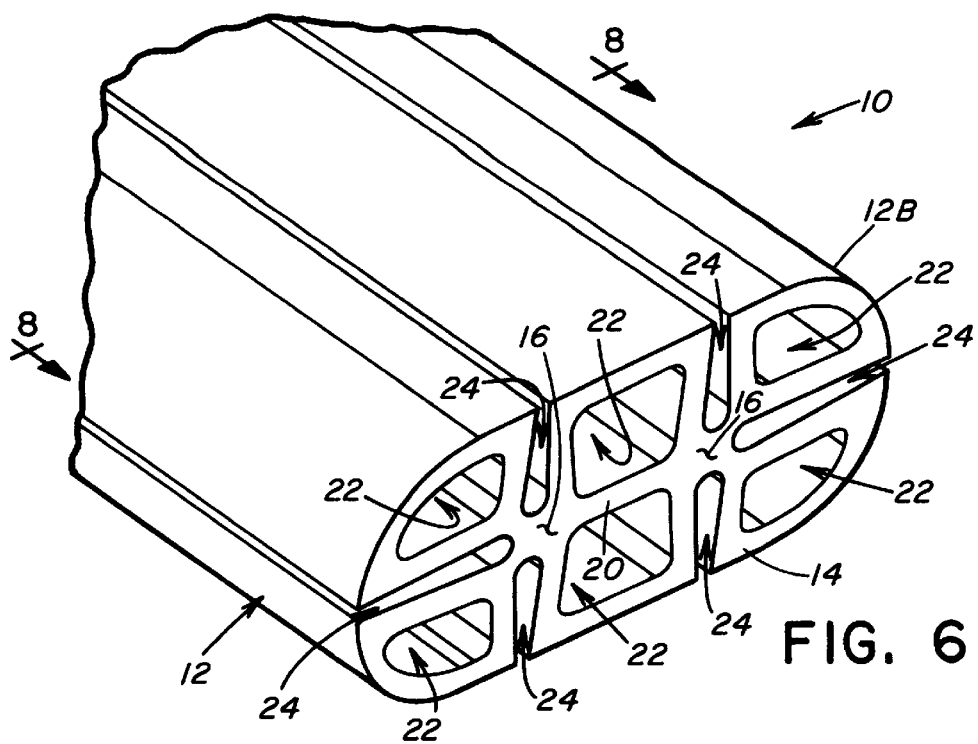
FIG. 6 is a fragmentary perspective view of the wound drain device of the present invention having a substantially oblong configuration in cross-section.
Figure 7:
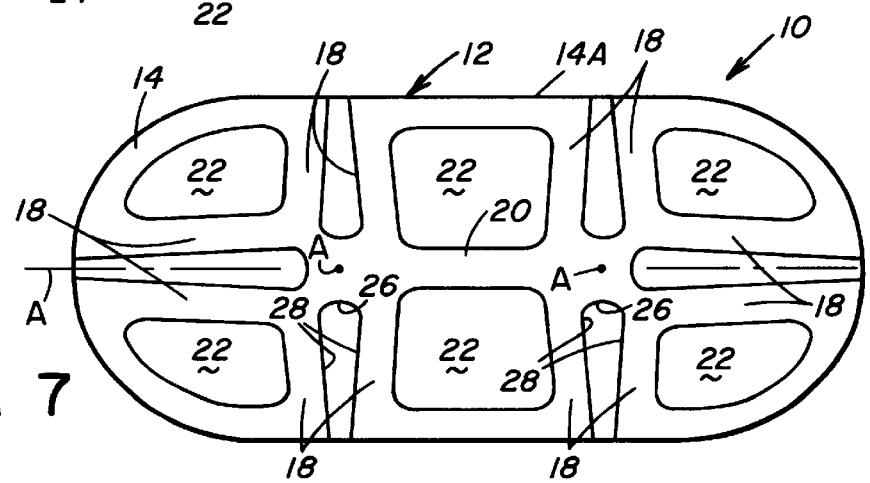
FIG. 7 is an enlarged end elevational view of the device shown in FIG. 6.

Referring to the drawings and particularly to FIGS. 1, 2, 6 and 7, there is illustrated an implantable wound drain device of the present invention, generally designated 10, for implantation into and drainage of fluid from a surgical site or wound of a patient. The device 10 is provided in two configurations, a first configuration in which the device 10 is generally round in cross-section, as shown in FIGS. 1 and 2, and a second configuration in which the device 10 is generally flattened or oblong in cross-section, as shown in FIGS. 6 and 7.

Figure 8:
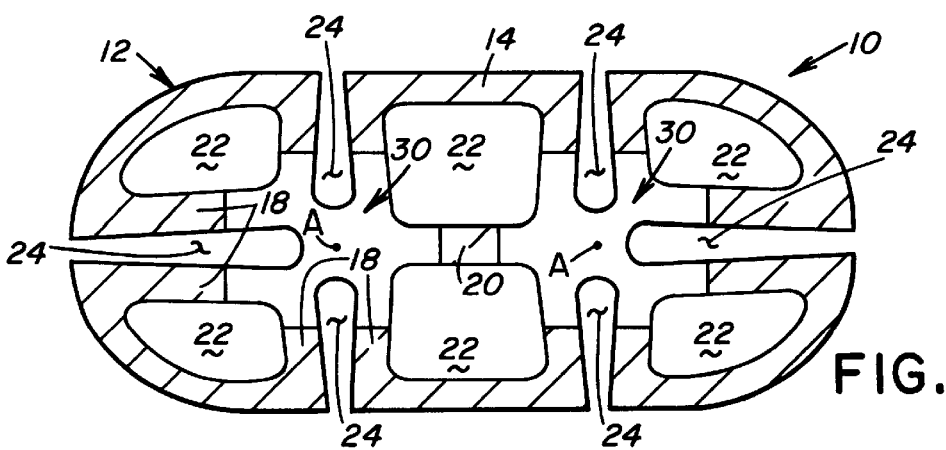
FIG. 8 is an enlarged cross-sectional view of the device taken along line 6—6 of FIG. 6 showing one form of the interior portals in the device.

Basically, the wound drain device 10 includes an elongated tubular body 12 having an annular outer wall 14 and opposite distal and proximal ends 12A 12B, a central core 16 disposed within and spaced radially inwardly from the outer wall 14, and a plurality of radial inner walls 18 disposed within the outer wall 14 and extending between and connected, preferably integrally, to the central core 16 and the outer wall 14. In the case of the first configuration of the device 10 of FIGS. 1–5, the annular outer wall 14 is generally round in cross-sectional shape and the central core 16 defines a single longitudinal axis A in the tubular body 12, whereas in the case of the second configuration of the device 10 of FIGS. 6–8, the annular outer wall 14 is generally oblong in cross-sectional shape and the central core 16 defines a pair of longitudinal axes A in the body 12 being laterally spaced in parallel relation to one another by an interior septum-like wall 20. Four inner walls 18 are shown, although other numbers of inner walls can be employed.

The tubular body 12 is manufactured by any suitable conventional fabrication technique, such as extrusion, and is made of a substantially pliable material such as low durameter (40–70 Shore A) plastic or silicone. The tubular body 12 generally has three sizes (10 Fr., 15 Fr., 19 Fr.) but can have any other suitable size. The oblong body 12 generally has two sizes (7 mm and 10 mm) but can have any other suitable size, as well.

The wound drain device 10 also includes a plurality of elongated enclosed lumens 22 which extend the length of the tubular body 12 between opposite distal and proximal ends 12A, 12B thereof and are formed by pairs of the inner walls 18 together with the outer wall 14. In the case of the second configuration of FIGS. 6–8, an extra pair of lumens 22 are formed by pairs of the inner walls 18 together with the outer wall 14 and the septum-like wall 20. The lumens 22 are circumferentially spaced from one another about and extend along the longitudinal axis A (or respective ones of the pair of longitudinal axes A in FIGS. 6–8) such that the inner walls 18 are disposed between adjacent pairs of the lumens 22. In the case of the tubular body 12 in the first configuration of FIGS. 1–5, the elongated lumens 22 are generally triangular-shaped in cross-section. In the case of the tubular body 12 in the second configuration of FIGS. 6–8, the elongated lumens 22 at the opposite sides of the body 12 are generally triangular-shaped in cross-section whereas the elongated lumens 22 at the middle of the body are generally rectangular-shaped in cross-section.

Referring to FIGS. 4–6 and 8–10, the wound drain device further includes a plurality of elongated open narrow ducts 24 extending the length of the tubular body 12 between opposite distal and proximal ends 12A, 12B thereof. Each inner wall 18 has one of the elongated narrow ducts 24 defined therein extending along the respective longitudinal axis A and extending outwardly from the central core 16 to the outer wall 14. Each duct 24 has an entrance 24A defined through the outer wall 14 to an exterior surface 14A thereof to permit fluid flow from the wound site located exteriorly of the outer wall 14 through the entrance 24A and into the duct 24. Thus, each duct 24 is disposed in a respective one of the inner walls 18 disposed between the adjacent pairs of lumens 22.

More particularly, each of the open narrow ducts 24 is formed by an interior base surface 26 and a pair of opposing interior side surfaces 28 defined in a respective one of the inner walls 18. The interior base surface 26 has a generally shallow U-shape in cross section, is located adjacent to the central core 16 and extends along the respective longitudinal axis A. The opposing interior side surfaces 28 are generally flat and extend in the direction along the respective longitudinal axis A and also extend outwardly from opposite edges of the interior base surface 26 to the exterior surface 14A of the outer wall 14. At the exterior surface 14A of the outer wall 14, the outer edges of the opposing interior side surfaces 28 define therebetween the elongated entrance 24A to the duct 24. Furthermore, each of the ducts 24 has a maximum width W1 between the opposing interior side surfaces 28 which is substantially smaller than a maximum width W2 of each of the lumens between the respective adjacent pairs of the inner walls 18. In addition, the opposite interior side surfaces 28 of each duct 24 preferably (although not necessarily; they can be parallel) converge toward one another as they extend outwardly from the interior base surface 26 to the entrance 24A of the duct 24. Therefore, the maximum width W1 between the interior side surfaces 28 adjacent to the interior base surface 26 is greater than the width W3 between the interior side surfaces 28 at the entrance 24A of the duct 24. This convergence of the interior opposing side surfaces 28 of each duct 24 is intended to provide sufficient access for fluid flow to enter the open narrow ducts 24 but limited access for tissue growth to enter the ducts. It will be noted that in the case of the first configuration of FIGS. 1–5 each opposing pair of the ducts 24 is bisected by the same plane of symmetry P while in the case of the second configuration of FIGS. 6–8 the opposite end pair of ducts 24 are bisected by the same plane of symmetry P.

In a first embodiment of the wound drain device 10 shown in FIGS. 1 and 2, where a combination of deep and shallow suction-induced drainage of fluids is desired, there is no or at least very little cross communication provided between the enclosed lumens 22 and open ducts 24. Thus, the application of suction to the lumens 22 and ducts 24 at the proximal end 12B of the device 10 draws a "deep" suction-induced drainage via the lumens 22 from the distal end 12A to the proximal end 12B of the device 10 and "shallow" suction-induced drainage via the open ducts 24 along the length of the device 10.

Figure 3:
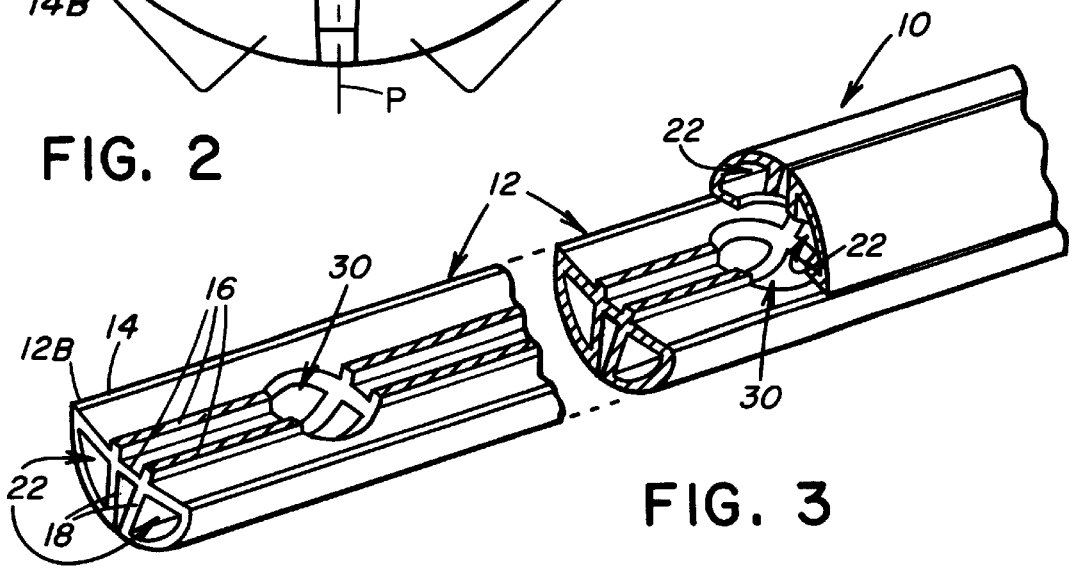
FIG. 3 is a perspective view with portions broken away and sectioned of a second embodiment of the wound drain device having longitudinally spaced internal portals and also having a central lumen in addition to the perimetrically arranged lumens.
Figure 4:
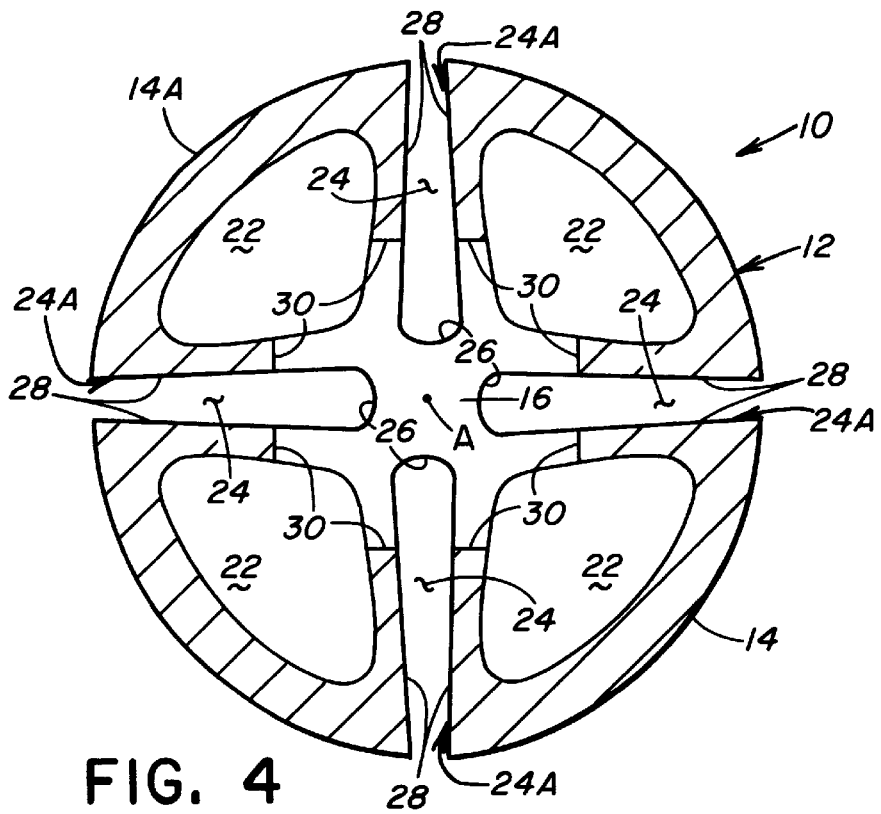
FIG. 4 is an enlarged cross-sectional view of the wound drain device showing one form of the interior portals in the device.
Figure 5:
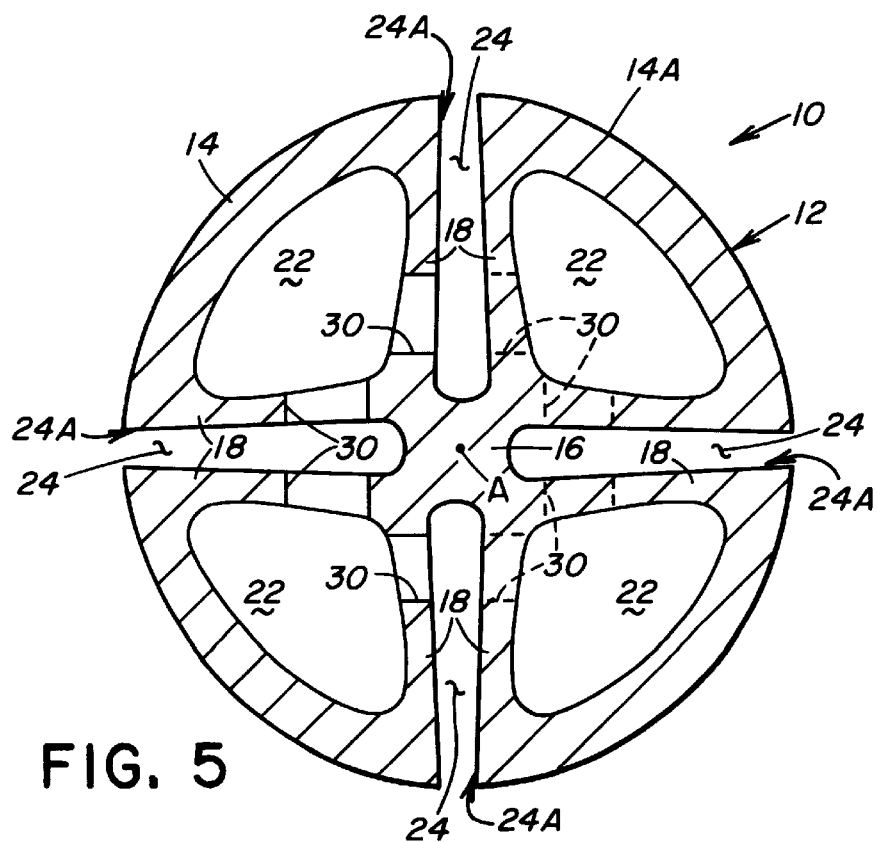
FIG. 5 is another enlarged cross-sectional view of the device similar to that of FIG. 4 but showing an alternative form of the interior portals in the device.

On the other hand in a second embodiment of the wound drain device 10 shown in FIGS. 3–5 where it is more desirable to distribute the suction substantially uniformly along the length of the device 10, the device 10 is provided with a cross flow communication providing means in the form of at least one and preferably a plurality of interior portals 30 spaced apart from each other and defined through the inner walls 18 and preferably also through the central core 16. The interior portals 30 are thus disposed closer to the interior base surface 26 of each duct 24 and to the inner end of each lumen 22 than to the entrances 24A of the ducts 24 and the portions 14B of the outer wall 14 enclosing the lumens 22. At such interior locations, the portals 30 serve to offset or displace access to the lumens 22 from the entrances 24A of the ducts 24 over distances sufficiently long to prevent growth of tissue into the lumens 22. While it is preferred to make the portals 30 intersect or cut through the central core 16 as well as the inner walls 18 as shown in FIG. 4, alternatively the portals 30 can be made through the inner walls 18 only, alternating from one side of the longitudinal axis A of central core 16 to an opposite side thereof as shown in FIG. 5.

Thus, the entrances 24A of the narrow ducts 24 through the outer wall 14 permit fluid flow from the wound site exteriorly of the drain 10 through the entrances 24A into the duct 24. The interior portals 30, which are not exposed at the exterior surface 14A of the outer wall 14 of the drain 10, then provide multiple collateral drainage paths for fluid flow from the ducts 24 to the exteriorly enclosed lumens 22 in the event clogging of any of the lumens 22 should occur at any specific location therealong. While the ducts 24 provide communication of fluids from the wound into the drain 10, the ducts 24 provide a means of offsetting the tissue from the interior portals 30 which minimizes the effects of tissue ingrowth by reducing the ability of the tissue to progress into the portals 30. The spacing of the portals 30 longitudinally along the axis A of the drain device 10 produces a substantially even distribution of suction over the length of the device.

Figure 9:
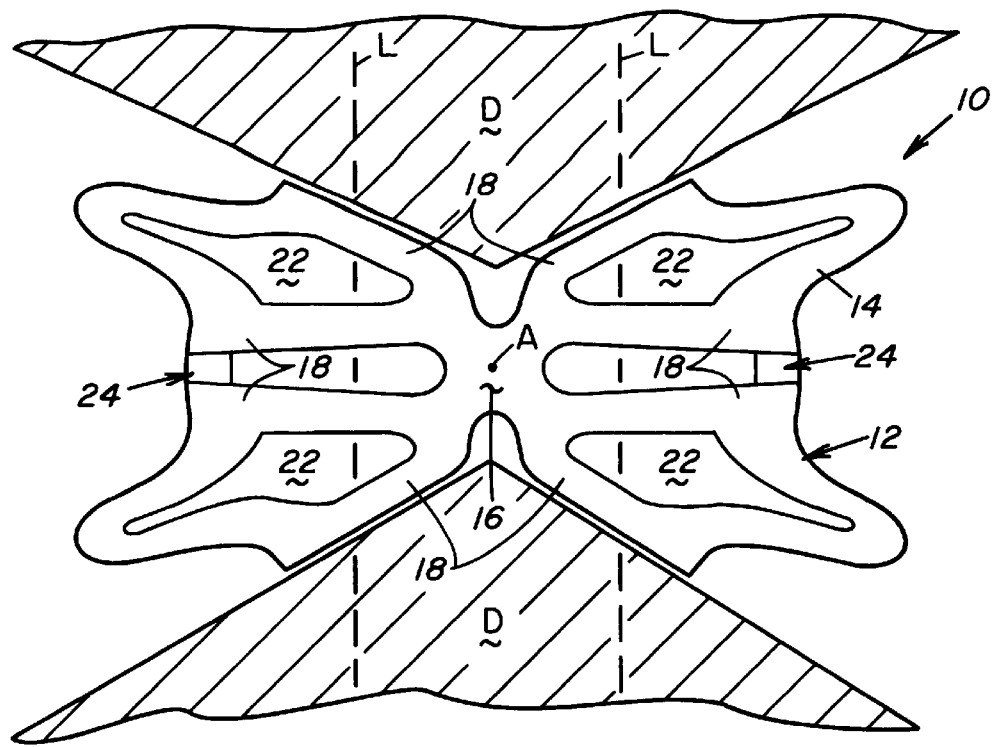
FIG. 9 is an enlarged end elevational view showing formation of the portals in the device of FIG. 1.
Figure 10:
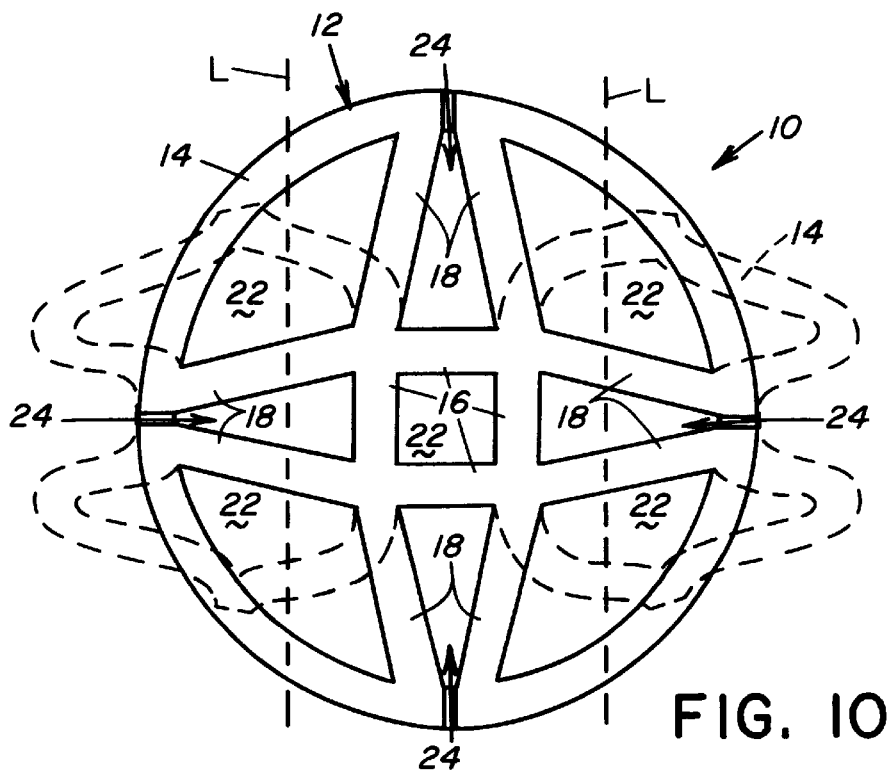
FIG. 10 is an enlarged end elevational view showing formation of the portals in the device of FIG. 3.

Referring to FIGS. 9 and 10, there is illustrated an exemplary technique for making the portals 30 in the interior of the tubular body 12 of the drain device 10. FIG. 9 shows the device 10 having a solid central core 16 in the body 12 while FIG. 10 shows the device 10 having a hollow central core 16 wherein an elongated lumen 22 is formed therewithin and extends along the longitudinal axis A of the central core 16. During a secondary operation following extrusion of the device 10, a pair of opposing wedge-shaped flatting dies D (shown only in FIG. 9) are used to spread open an opposing pair of the ducts 24 on the same plane of symmetry P. (The dashed lines in FIG. 10 depict the shape of the device after such spreading by the dies.) Thereafter, the portals 30 are punched by conventional dies (not shown) preferably through the inner walls 18 and central core 16, removing the material located between the parallel dashed lines L, such that all lumens 22 and ducts 24 are thereby traversed to provide for maximum number of collateral drainage paths. Alternatively, the portals 30 can be formed such that the longitudinal axis A is not intersected and the portals alternate sides of the axis. The latter method is designed to improve the tensile strength of the drain device. In the case of the second configuration of the drain device of FIGS. 6–8, the portals are formed on each of the axes A separately from the other.

Referring again to FIG. 1, the above-described elements of the drain device 10 constitute an implantable segment 31 of a wound drain which is adapted to be used in combination with a transition segment 32 for receiving fluid draining from the implantable segment 31 and with a unitary segment 34 for receiving fluid draining from the transition segment 32. However, only the implantable segment 31 is actually disposed within the wound site. All segments of the wound drain can be manufactured in a continuous extrusion process. When the required length of the implantable segment 31 has been extruded the transition segment 32 is then formed. As the extrusion process progresses, the entrances 24A to the ducts 24 are filled with material to form the outer wall 14 with an uninterrupted perimeter. The lumens now created by the enclosed ducts in the transition segment 32 are in communication with the ducts 24 of the implantable segment 31. When the transition segment 32 is complete, the extrusion die discontinues the central core 16 and radial inner walls 18 such that only one lumen remains and it is in communication with all transitional lumens. The single remaining lumen in the unitary segment 34 is in the form of a cylindrical tube. This mode of extrusion has been called "unitary" extrusion. For the drain device 10 having the oblong shape in cross-section, following the transition segment 32, the tubular segment may be attached via a hub (adapter). The tubular segment will be of sufficient length to provide effective connection to a suction source.

Other modifications to the drain device 10 can include changes in the extrusion technique without changes to the above-described elements of the drain device 10. An example of this may be an extrusion profile that is hubbed to a single lumen tube rather than produced by a unitary extrusion technique. Other modifications of the design may include variations in the number of lumens, ducts and/or portals. Additional modifications include variation in the shape of the portals 30. Their shape is not restricted to circular.

In conclusion, the above-described elements provide an implantable wound drain device 10 which meets all existing requirements for a surgical drain. The device (1) minimizes access of the tissue to the portals 30, (2) evenly distributes suction over the length of the implanted segment 31 of the drain device 10, (3) provides collateral drainage paths around an occluded lumen, and (4) has the structural integrity to remain patent in a wound drainage application.

It is thought that the present invention and its advantages will be understood from the foregoing description and it will be apparent that various changes may be made thereto without departing from the spirit and scope of the invention or sacrificing all of its material advantages, the form hereinbefore described being merely preferred or exemplary embodiment thereof.

I claim:

1. A wound drain device for implantation into and for drainage of fluid from a wound of a patient, said device comprising:

(a) an elongated annular outer wall defining an exterior surface;

(b) an elongated central core defining at least one longitudinal axis and being disposed within and spaced radially inwardly from said outer wall; and (c) a plurality of elongated radial inner walls disposed within said outer wall and extending along, outwardly from, and circumferentially spaced about said longitudinal axis, said inner walls further extending between and connected to said central core and said outer wall such that said inner walls together with said outer wall form a plurality of elongated enclosed lumens for draining fluids therefrom from the wound, said lumens circumferentially being spaced from one another about and extending along said longitudinal axis such that said inner walls are disposed between said lumens;

(d) each of said inner walls having an elongated open duct defined therein extending along said longitudinal axis such that each of said ducts is in a respective one of said inner walls disposed between said lumens, each of said ducts being formed by an interior base surface defined in said respective one inner wall adjacent to said central core and by a pair of opposing interior side surfaces defined in said respective one inner wall so as to extend from said interior base surface to said exterior surface of said outer wall and define an elongated entrance to said duct through said outer wall to permit fluid flow from the wound exteriorly of said outer wall through said entrance and into said duct, each of said ducts having a maximum width between said opposing interior side surfaces which is substantially smaller than a maximum width of each of said lumens between said inner walls.

2. The device of claim 1 wherein said maximum width of each of said ducts is located adjacent to said interior base surface thereof, said width of each of said ducts diminishing toward said entrance thereto.

3. The device of claim 1 further comprising:

means for providing cross flow communication between said open ducts and enclosed lumens adjacent to said central core so as to produce a relatively uniform distribution of suction along said longitudinal axis and to define and thereby permit fluid flow along multiple drainage paths from exteriorly of said outer wall through said entrances of said ducts into and through said ducts and, via said cross flow communication providing means, into said lumens in the event of clogging of any of said lumens at a specific location therealong.

4. The device of claim 3 wherein said cross flow communication providing means is disposed closer to said interior base surface of each of said ducts than to said entrances thereof through said outer wall so as to displace access, via said cross flow communication providing means, to said lumens from said entrances of said ducts over distances sufficiently long to prevent growth of tissue into said lumens.

5. The device of claim 3 wherein said cross flow communication providing means is disposed along of said longitudinal axis of central core alternately at one side and an opposite side thereof.

6. The device of claim 3 wherein said cross flow communication providing means includes a plurality of interior portals spaced apart from each other and defined through said inner walls adjacent to said central core, said portals for providing said multiple drainage paths for fluid flow from said ducts to said lumens.

7. The device of claim 6 wherein said portals are disposed closer to said interior base surface of said ducts than to said outer wall and transverse across said central core and each of said ducts and said lumens for providing fluid flow through said central core between said ducts and said lumens to thereby provide said drainage paths for fluid flow.

8. The device of claim 1 wherein said opposite interior side surfaces of each of said ducts converge toward one another extending in a direction outwardly from said interior base surface to said entrance of said duct and thereby said width between said interior side surfaces adjacent to said interior base surface is greater than the width between said interior side surfaces at said entrance of said duct, whereby convergence of said interior opposing side surfaces of said duct provides sufficient access for fluid flow to enter said duct but limited access for tissue growth to enter said ducts.

9. The device of claim 1 further comprising:

an elongated lumen formed within, and extending along said longitudinal axis of, said central core.

10. A wound drain device for implantation into and for drainage of fluid from a wound of a patient, said device comprising:

(a) an elongated annular outer wall defining an exterior surface, said outer wall having a substantially round shape in cross-ssection;

(b) an elongated central core defining at least one longitudinal axis and being disposed within and spaced radially inwardly from said outer wall;

(c) a plurality of elongated radial inner walls disposed within said outer wall and extending along, outwardly from, and circumferentially spaced about said longitudinal axis, said inner walls further extending between and connected to said central core and said outer wall such that said inner walls together with said outer wall form a plurality of elongated enclosed lumens for draining fluids therefrom from the wound, said lumens being circumferentially spaced from one another about and extending along said longitudinal axis such that said inner walls are disposed between said lumens;

(d) each of said inner walls having an elongated open duct defined therein extending along said longitudinal axis such that each of said ducts is in a respective one of said inner walls disposed between said lumens, each of said ducts being formed by an interior base surface defined in said respective one inner wall adjacent to said central core and by a pair of opposing interior side surfaces defined in said respective one inner wall so as to extend from said interior base surface to said exterior surface of said outer wall and define an elongated entrance to said duct through said outer wall to permit fluid flow from the wound exteriorly of said outer wall through said entrance and into said duct, each of said ducts having a maximum width between said opposing interior side surfaces which is substantially smaller than a maximum width of each of said lumens between said inner walls; and (e) a plurality of interior portals spaced apart from each other and defined through said inner walls adjacent to said central core for providing flow communication between said ducts and lumens adjacent to and at locations spaced along said central core to produce a relatively uniform distribution of suction along said longitudinal axis and to define and thereby provide multiple drainage paths for fluid flow from exteriorly of said outer wall through said entrances of said ducts into and through said ducts and, via said spaced portals, into said lumens in the event of clogging of any of said lumens at a specific location therealong.

11. The device of claim 10 wherein said maximum width of each of said ducts is located adjacent to said interior base surface thereof, said width of each of said ducts diminishing toward said entrance thereto.

12. The device of claim 10 wherein said portals are disposed closer to said interior base surface of each of said ducts than to said entrances thereof through said outer wall so as to displace access, via said portals, to said lumens from said entrances of said ducts over distances sufficiently long to prevent growth of tissue into said lumens.

13. The device of claim 10 wherein said portals are disposed closer to said interior base surface of said ducts than to said outer wall and transverse across said central core and each of said ducts and said lumens for providing fluid flow through said central core between said ducts and said lumens to thereby provide said multiple drainage paths for fluid flow.

14. The device of claim 10 wherein said opposite interior side surfaces of each of said ducts converge toward one another extending in a direction from said interior base surface outwardly to said entrance of said duct and thereby said width between said interior side surfaces adjacent to said interior base surface is greater than the width between said interior side surfaces at said entrance of said duct, whereby convergence of said interior opposing side surfaces of said duct provides sufficient access for fluid flow to enter said duct but limited access for tissue growth to enter said ducts.

15. The device of claim 10 further comprising:

an elongated lumen formed within, and extending along said longitudinal axis of, said central core.

* * * * *